(12) United States Patent
Bomzon et al.

(10) Patent No.: US 11,911,612 B2
(45) Date of Patent: Feb. 27, 2024

(54) USING POWER LOSS DENSITY AND RELATED MEASURES TO QUANTIFY THE DOSE OF TUMOR TREATING FIELDS (TTFIELDS)

(71) Applicant: Novocure GmbH, Root (CH)

(72) Inventors: Zeev Bomzon, Kiryat Tivon (IL); Hadas Sara Hershkovich, Kiryat Motzkin (IL); Noa Urman, Pardes Hanna Carcur (IL); Ariel Naveh, Haifa (IL); Shay Levi, Tel Aviv-Jaffa (IL)

(73) Assignee: Novocure GmbH, Root (CH)

( * ) Notice: Subject to any disclaimer, the term of this patent is extended or adjusted under 35 U.S.C. 154(b) by 955 days.

(21) Appl. No.: 16/515,311

(22) Filed: Jul. 18, 2019

(65) Prior Publication Data
US 2020/0023179 A1     Jan. 23, 2020

Related U.S. Application Data

(60) Provisional application No. 62/833,983, filed on Apr. 15, 2019, provisional application No. 62/754,901, (Continued)

(51) Int. Cl.
*A61N 1/36* (2006.01)
*G16H 30/40* (2018.01)
*A61B 5/055* (2006.01)

(52) U.S. Cl.
CPC ......... *A61N 1/36002* (2017.08); *G16H 30/40* (2018.01); *A61B 5/055* (2013.01)

(58) Field of Classification Search
CPC ........ G16H 50/50; G16H 20/40; G16H 40/63; G16H 70/20; G16H 30/40; G16H 20/30;
(Continued)

(56) References Cited

U.S. PATENT DOCUMENTS 6,868,289 B2   3/2005   Palti
7,016,725 B2   3/2006   Palti
(Continued)

FOREIGN PATENT DOCUMENTS

WO     2011047387 A2    4/2011

OTHER PUBLICATIONS

International Search Report and Written Opinion issued in application No. PCT/IB2019/056181 dated Jan. 8, 2020.

*Primary Examiner* — Golam Sorowar
(74) *Attorney, Agent, or Firm* — Potomac Law Group, PLLC

(57) ABSTRACT

The planning of treatment using tumor treating fields (TT-Fields) in a portion of a subject's body (e.g., the subject's head) can be improved by obtaining an image of the body portion, and generating, based on the image, a 3D model of electrical conductivity. A target volume within the 3D model is identified, and a set of model electrodes is added to the 3D model at given locations. Then, for each voxel in the target volume, the power loss density (PLD) that will be present when TTFields are eventually applied is determined. The same process is repeated for a plurality of different electrode locations. Finally, the set of electrode locations that yielded the best PLD is selected, and a description of those locations is output.

19 Claims, 7 Drawing Sheets

Related U.S. Application Data filed on Nov. 2, 2018, provisional application No. 62/700,080, filed on Jul. 18, 2018.

(58) Field of Classification Search
CPC ........ G16H 50/20; G16H 30/20; G16H 50/70; G16H 40/60; G16H 10/60; G16H 40/00; G16H 40/67; G16H 50/00; G16H 20/70; A61B 5/055; A61B 34/10; A61B 2034/104; A61B 2034/105; A61B 2018/00577; A61B 18/1492; A61B 2034/107; A61B 34/20; A61B 2018/00613; A61B 2018/00875; A61B 5/316; A61B 5/053; A61B 5/0536; A61B 18/1477; A61B 2090/103; A61B 18/1206; A61B 5/065; A61B 5/287; A61B 6/032; A61B 90/37; A61B 6/12; A61B 2018/0016; A61B 2562/043; A61B 6/03; A61B 34/25; A61B 5/063; A61B 5/0042; A61B 5/0538; A61B 5/068; A61B 5/349; A61N 1/36185; A61N 1/37247; A61N 1/36082; A61N 1/36128; A61N 1/0551; A61N 1/0476; A61N 1/36025; A61N 1/0456; A61N 1/40; A61N 1/0412; A61N 1/0529; A61N 1/36002; A61N 1/0541; A61N 1/32; A61N 1/36067; A61N 1/36071; A61N 1/327; A61N 1/37264; A61N 1/08; A61N 1/36039; A61N 1/3605; A61N 1/0424; A61N 1/0484; A61N 1/326; A61N 1/36014; A61N 1/36031; A61N 1/36038; A61N 1/36139
See application file for complete search history.

(56) References Cited

U.S. PATENT DOCUMENTS

| | | | |
|---|---|---|---|
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 2003/0191506 A1 | 10/2003 | Shloznikov | |
| 2016/0055304 A1* | 2/2016 | Russell | A61B 6/5247 705/3 |
| 2017/0120041 A1* | 5/2017 | Wenger | A61B 5/05 |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0153437 A1* | 6/2018 | Schwartz | A61B 5/287 |
| 2018/0160933 A1 | 6/2018 | Urman et al. | |
| 2018/0202991 A1 | 7/2018 | Giladi et al. | |
| 2019/0117956 A1 | 4/2019 | Wenger et al. | |
| 2019/0298982 A1 | 10/2019 | Story et al. | |
| 2019/0307781 A1 | 10/2019 | Krex et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0016399 A1 | 1/2020 | Kaynan et al. | |

* cited by examiner

USING POWER LOSS DENSITY AND RELATED MEASURES TO QUANTIFY THE DOSE OF TUMOR TREATING FIELDS (TTFIELDS)

CROSS REFERENCE TO RELATED APPLICATIONS

This Application claims the benefit of U.S. Provisional Applications 62/700,080 (filed Jul. 18, 2018), 62/754,901 (filed Nov. 2, 2018), and 62/833,983 (filed Apr. 15, 2019), each of which is incorporated herein by reference in its entirety.

BACKGROUND

Tumor Treating Fields, or TTFields, are low intensity 1-3 V/cm) alternating electric fields within the intermediate frequency range (100-300 kHz) that inhibit cancer cell growth. This non-invasive treatment targets solid tumors and is described in U.S. Pat. No. 7,565,205, which is incorporated herein by reference in its entirety. TTFields are approved for the treatment of glioblastoma, and may be delivered, for example, via the Optune™ system. Optune™ includes a field generator and two pairs of transducer arrays (i.e., electrode arrays) that are placed on the patient's shaved head. One pair of electrodes is located to the left and right (LR) of the tumor, and the other pair of electrodes is located anterior and posterior (AP) to the tumor.

Preclinical studies have shown that TTFields' inhibitory effect increases with field intensity. The intensity of the electric field has historically been used to quantify the dose of TTFields, and the positioning of the electrodes has historically been adjusted in order to optimize the intensity of the electric field.

One example of a prior art approach for determining where to position the electrodes is described in U.S. Pat. No. 10,188,851, which describes generating a 3D map of conductivity directly from MRI-derived measurements without segmenting the anatomic volume into tissue types. Model electrodes are then placed at different positions on this 3D map, and the electric field intensities resulting from each of these different electrode layouts are analyzed. The electrode layout that yielded the best distribution of electric field intensities is selected and subsequently used to apply TTFields to the patient.

SUMMARY OF THE INVENTION

One aspect of the invention is directed to a first method of planning a treatment using alternating electric fields at a given frequency in a portion of a subject's body. The first method comprises (a) obtaining at least one image of the portion; (b) generating, based on the obtained at least one image, a 3D model of electrical conductivity or resistivity at the given frequency within the portion; and (c) identifying a target volume within the 3D model, the target volume including a plurality of voxels. The first method also comprises (d) adding a first set of model electrodes to the 3D model, with the first set of model electrodes positioned at a first set of locations with respect to the 3D model; (e) determining, for each of the voxels in the target volume, a power loss density that will be present when the first set of model electrodes positioned at the first set of locations is used to impose an alternating electric field in the target volume; (f) adding a second set of model electrodes to the 3D model, with the second set of model electrodes positioned at a second set of locations with respect to the 3D model; and (g) determining, for each of the voxels in the target volume, a power loss density that will be present when the second set of model electrodes positioned at the second set of locations is used to impose an alternating electric field in the target volume. The first method also comprises (h) selecting a set of locations for the electrodes based on results of step (e) and step (g).

Some instances of the first method further comprise outputting a description of the selected set of locations.

In some instances of the first method, step (e) and step (g) each comprises determining, for each of the voxels in the target volume, an electric field intensity that will be present when a respective set of model electrodes positioned at a respective set of locations is used to impose an alternating electric field in the target volume; and determining a respective power loss density for each voxel in the target volume based on the conductivity of the 3D model at the voxel and the electric field intensity at the voxel. in some of these instances, the power loss density for each voxel in the target volume is determined using the formula $L=\frac{1}{2}\sigma|E|^2$, where $\sigma$ is the conductivity of the 3D model at the voxel and $|E|$ is the electric field intensity at the voxel.

In some instances of the first method, step (h) comprises selecting the set of locations that maximizes average power loss density in the target volume. In some instances of the first method, step (h) comprises selecting the set of locations that maximizes the lowest power loss density in the target volume.

Some instances of the first method further comprise (h) adding a third set of model electrodes to the 3D model, with the third set of model electrodes positioned at a third set of locations with respect to the 3D model; and (i) determining, for each of the voxels in the target volume, a power loss density that will be present when the third set of model electrodes positioned at the third set of locations is used to impose an alternating electric field in the target volume. In these instances, the selecting comprises selecting a set of locations for the electrodes based on results of step (e), step (g), and step (i).

In some instances of the first method, the at least one image of the portion comprises an MRI image of the portion.

Some instances of the first method further comprise affixing a plurality of electrodes to the subject's body at the selected locations; and applying an AC voltage between the affixed electrodes, so as to impose the alternating electric field in the target volume.

Another aspect of the invention is directed to a second method of planning a treatment using alternating electric fields at a given frequency in a portion of a subject's body. The second method comprises (a) obtaining at least one image of the portion; (b) generating, based on the obtained at least one image, a 3D model of electrical conductivity or resistivity at the given frequency within the portion; and (c) identifying a target volume within the 3D model, the target volume including a plurality of voxels. The second method also comprises (d) adding a first set of model electrodes to the 3D model, with the first set of model electrodes positioned at a first set of locations with respect to the 3D model; (e) determining, for each of the voxels in the target volume, the smaller one of first and second power loss densities that will be present when the first set of model electrodes positioned at the first set of locations is used to impose an alternating electric field in the target volume with first and second orientations, respectively; (f) adding a second set of model electrodes to the 3D model, with the second set of model electrodes positioned at a second set of locations with respect to the 3D model; and (g) determining, for each of the voxels in the target volume, the smaller one of first and second power loss densities that will be present when the second set of model electrodes positioned at the second set of locations is used to impose an alternating electric field in the target volume with first and second orientations, respectively. The second method also comprises (h) selecting a set of locations for the electrodes based on results of step (e) and step (g).

Some instances of the second method further comprise outputting a description of the selected set of locations.

In some instances of the second method, step (e) and step (g) each comprises determining, for each of the voxels in the target volume, a first orientation electric field intensity that will be present when a respective set of model electrodes positioned at a respective set of locations is used to impose an alternating electric field in the target volume with the first orientation; determining a respective first-orientation power loss density for each voxel in the target volume based on the conductivity of the 3D model at the voxel and the first orientation electric field intensity at the voxel; determining, for each of the voxels in the target volume, a second orientation electric field intensity that will be present when the respective set of model electrodes positioned at the respective set of locations is used to impose an alternating electric field in the target volume with the second orientation; determining a respective second-orientation power loss density for each voxel in the target volume based on the conductivity of the 3D model at the voxel and the second orientation electric field intensity at the voxel; and selecting, for each of the voxels in the target volume, the smaller of the respective first-orientation power loss density and the respective second-orientation power loss density. In some of these instances, the respective first-orientation power loss density and the respective second-orientation power loss density for each voxel in the target volume is determined using the formula $L=\frac{1}{2}\sigma|E|^2$, where $\sigma$ is the conductivity of the 3D model at the voxel and E is the respective electric field intensity at the voxel.

In some instances of the second method, step (h) comprises selecting the set of locations that maximizes average power loss density in the target volume. in some instances of the second method, step (h) comprises selecting the set of locations that maximizes the lowest power loss density in the target volume.

Some instances of the second method further comprise (h) adding a third set of model electrodes to the 3D model, with the third set of model electrodes positioned at a third set of locations with respect to the 3D model; and (i) determining, for each of the voxels in the target volume, the smaller one of first and second power loss densities that will be present when the third set of model electrodes positioned at the third set of locations is used to impose an alternating electric field in the target volume with first and second orientations, respectively. In these instances, the selecting comprises selecting a set of locations for the electrodes based on results of step (e), step (g), and step (i).

In some instances of the second method, the at least one image of the portion comprises an MRI image of the portion.

Some instances of the second method further comprise affixing a plurality of electrodes to the subject's body at the selected locations; and applying an AC voltage between the affixed electrodes, so as to impose the alternating electric field in the target volume.

In some instances of the second method, the treatment using alternating electric fields is planned so that an average Local Minimum Power Density in the target volume is at least 1.0 mW/cm$^3$.

Another aspect of the invention is directed to a third method of planning a treatment using alternating electric fields at a given frequency in a portion of a subject's body. The third method comprises (a) obtaining at least one image of the portion; (b) generating, based on the obtained at least one image, a 3D model of electrical conductivity or resistivity at the given frequency within the portion; and (c) identifying a target volume within the 3D model, the target volume including a plurality of voxels. The third method also comprises (d) adding a first set of model electrodes to the 3D model, with the first set of model electrodes positioned at a first set of locations with respect to the 3D model; and (e) determining, for each of the voxels in the target volume, a power loss density that will be present when the first set of model electrodes positioned at the first set of locations is used to impose an alternating electric field in the target volume.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Electric field intensity quantifies the force that the electric field applies on intracellular objects (e.g., organelles). But when considering the dose of a physical modality such as TTFields, it is important to not only consider the forces at work but also the amount of energy transferred from the modality to the tissue (i.e., the work that the modality performs). This is because quantifying energy and work may provide a better description of the extent to which the physical modality alters the state of the objects on which it operates.

This application explains that power loss density of the electric field can advantageously be used to quantify the dose of TTFields in a target volume for any given set of electrode positions. Furthermore, the power loss density distribution can be analyzed for a plurality of different electrode positions, so that the electrode positions that yield the best power loss density distribution can be selected. TTFields are then applied to the patient using the selected set of electrode positions. This new approach stands in sharp contrast with the traditional approach in which the decision of where to position the electrodes was based on simulations of the intensity of the electric field.

The power loss density of an electric field, L, is defined as $$L = 1/2\sigma |E|^2$$

where $\sigma$ is the conductivity of tissue and $|E|$ is the intensity of the electric field. This relationship is referred to herein as formula (1). Power loss density is measured in units of milliwatts per cubic centimeter (mW/cm$^3$).

To examine the distribution of TTFields power loss density when delivering TTFields to the brain, realistic patient head models were created based on MRIs of glioblastoma patients using the approach described in U.S. 2018/0160933, entitled "Treating Patients with TTFields with the Electrode Positions Optimized Using Deformable Templates," which is incorporated herein by reference in its entirety. The realistic head models specify the conductivity at each voxel in 3D space within the head, (including the brain, skull, and scalp), and any of a variety of alternative approaches for generating the 3D conductivity map of the relevant body portion could also be used (e.g., as described below in connection with step S22). After the realistic head models were obtained, numerical simulations were run to simulate positioning Optune™ electrodes on those realistic head models, and to simulate applying AC voltages to those electrodes using the Optune™ system in order to simulate the delivery of TTFields to those realistic head models. Of course, in alternative embodiments, different types of electrodes other than Optune™ electrodes) may be used, as long as the simulations are adjusted to account for the differences in the electrodes.

Figure 1A:
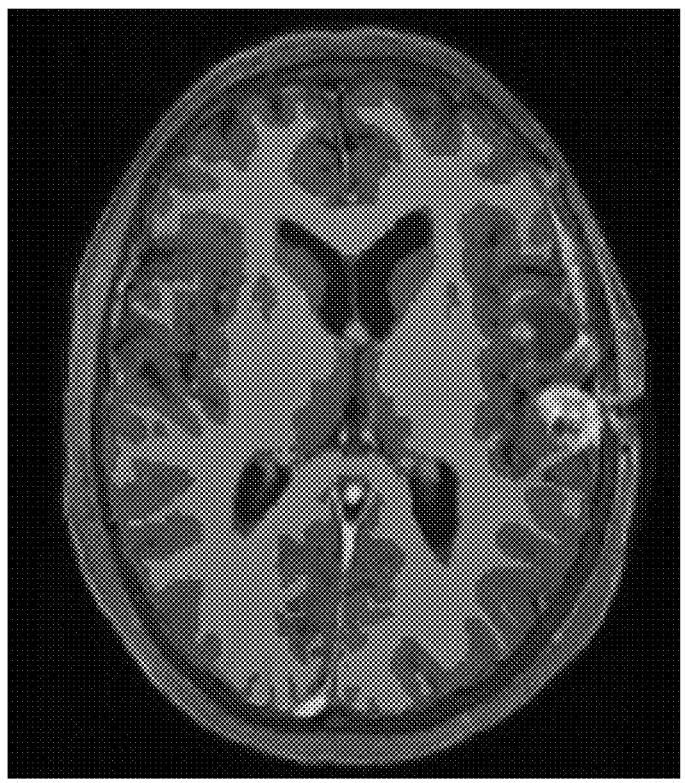
FIG. 1A depicts an axial slice through a computational model of a head.
Figure 1B:
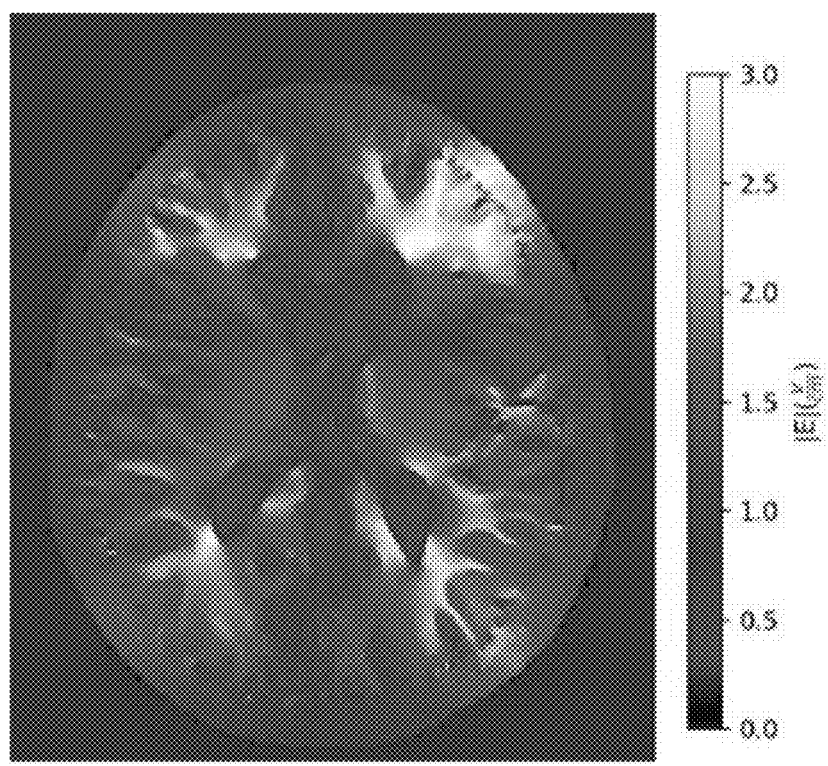
FIG. 1B depicts a corresponding distribution of electric field intensity for a given placement of electrodes on the model.
Figure 1C:
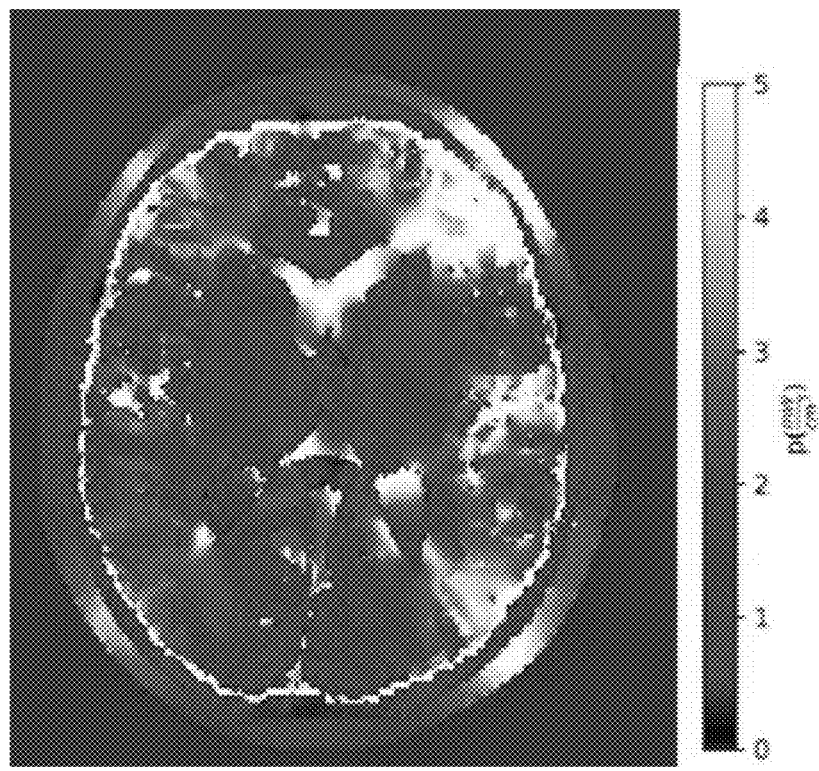
FIG. 1C depicts a corresponding distribution of power loss density for the same placement of electrodes.

The field intensity distribution and power loss density distribution within the models were calculated and compared, and FIGS. 1A-1C depict the results of those comparisons for a representative set of electrode locations. More specifically, FIG. 1A depicts an axial slice through a computational model that specifies the conductivity at each voxel within the relevant body portion. After models of the electrodes were positioned on the computational model (at the representative set of electrode locations) and simulated AC voltages were applied across those model electrodes, the intensity of the electric field (in V/cm) at each voxel was computed, resulting in the distribution of field intensity shown in FIG. 1B. The field intensity in FIG. 1B at each voxel was then mapped to a corresponding power loss density using formula (1) noted above, and the resulting power loss density distribution is shown in FIG. 1C. The field intensity distribution and power loss density distribution show some degree of correlation, but there are clear differences between the two distributions. More specifically, the electric field intensity (FIG. 1B) tends to increase in regions of low conductivity (e.g., white matter) and tends to be lowest in regions of a high conductivity (e.g. the ventricles and resection cavities). On the other hand, the power loss density (FIG. 1C) tends to increase in regions of higher conductivity. And within the ventricles and resection cavity, the power loss density can take on values comparable to those observed in other tissue types.

Figure 2:
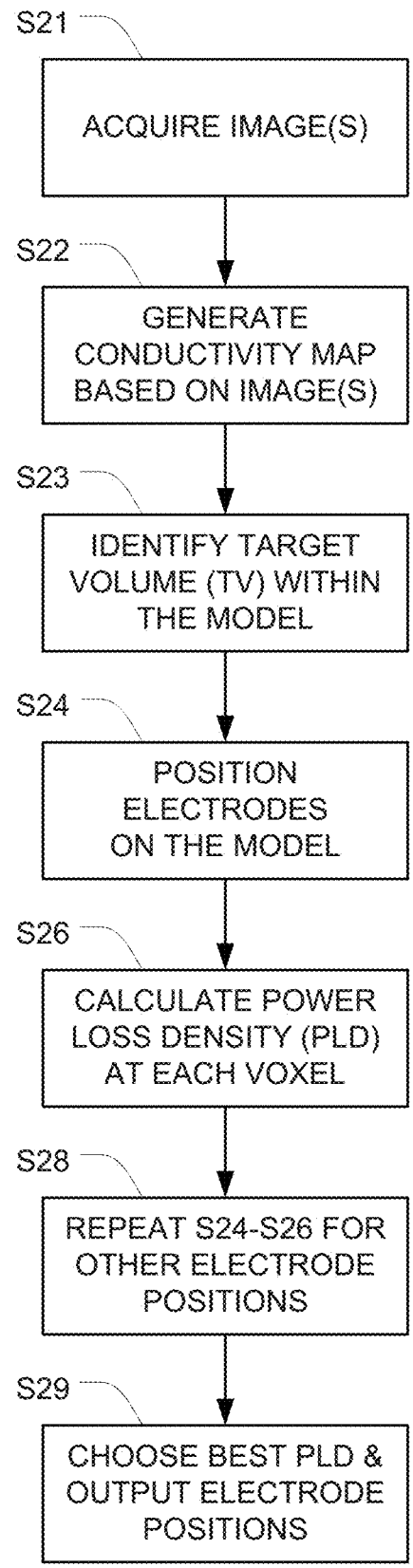
FIG. 2 is a flowchart of one example for planning a treatment using TTFields in a portion of a subject's body that relies on power loss density.

FIG. 2 is a flowchart of one example for planning a treatment using TTFields in a portion of a subject's body that relies on power loss density. This example begins in step S21, where the relevant images of the portion of the subject's body are obtained. These images could be one or more images of the body portion obtained using any imaging modality including but not limited to MRI, CT, etc. In some preferred embodiments, at least one MRI image is used.

Next, in step S22, a conductivity map of the body portion is generated based on the image(s) obtained in step S21. Note that because TTFields are alternating electric fields, and conductivity depends on frequency, the conductivity map should take into account the frequency at which the TTFields will ultimately be applied. The conductivity map is preferably a 3D model of electrical conductivity at the relevant frequency within the body portion. For example, since glioblastoma is treated using 200 kHz TTFields, a conductivity map for planning TTFields treatment of glioblastoma should specify the conductivity of each voxel at 200 kHz AC.

The conductivity map can be generated using a variety of approaches. For example, the conductivity map can be generated from MRI images using the approach described in U.S. Pat. No. 10,188,851, which is incorporated herein by reference in its entirety. Alternatively, the conductivity map could be generated by performing manual segmentation of MRI images (i.e., manually identifying the various tissue types such as white matter, gray matter, necrotic core, etc. in the MRI images), and assigning a suitable conductivity value to each of the relevant tissue types. A variety of alternative approaches for generating the conductivity map will be apparent to persons skilled in the relevant art. In order to create a good computational model, the use of high resolution images (e.g., with a resolution of at least 1 mm×1 mm×1 mm) is preferable. Lower resolution images may also be used, but will yield less accurate results. Note that while the embodiments described herein discuss mapping conductivity, alternative embodiments can provide similar results by mapping a different electrical property such as resistivity.

In step S23, the target volume is identified within the 3D model. The target volume includes a large number of voxels. In the context of glioblastoma, the target volume will typically be the region within the brain that contains the glioblastoma. In some embodiments, the target volume will be either the Gross Tumor Volume (GTV) or the Clinical Target Volume (CTV). The GTV is the gross demonstrable extent and location of the tumor, whereas the CTV includes the demonstrated tumors if present and any other tissue with presumed tumor. In many cases the CTV is found by defining a volume that encompasses the GTV and adding a margin with a predefined width around the GTV.

In order to identify the GTV or the CTV, it is necessary to identify the volume of the tumor within the MRI images. This can be performed either manually by the user, automatically, or using a semi-automatic approach in which user-assisted algorithms are used. When performing this task manually, MRI data could be presented to a user, and the user could be asked to outline the volume of the CTV on the data. The data presented to the user could be structural MRI data (e.g., $T_1$, $T_2$ data). The different MRI modalities could be registered onto each other, and the user could be presented with the option to view any of the datasets, and outline the CTV. The user could be asked to outline the CTV on a 3D volumetric representation of the MRIs, or the user could be given the option of viewing individual 2D slices of the data, and marking the CTV boundary on each slice. Once the boundaries have been marked on each slice, the CTV within the anatomic volume (and hence within the realistic model) can be found. In this case, the volume marked by the user would correspond to the GTV. In some embodiments, the CTV could then be found by adding margins of a predefined width to the GTN. Similarly, in other embodiments, the user might be asked to mark the CTV using a similar procedure.

Optionally, semi-automatic segmentation approaches of the MRI data may be implemented. In an example of these approaches, a user iteratively provides input into an algorithm (e.g., the location of the tumor on the images, roughly marking the boundaries of the tumor, demarcating a region of interest in which the tumor is located), which is then used by a segmentation algorithm. The user may then be given the option to refine the segmentation to improve the estimation of the CTV location and volume within the body-portion.

Whether using automatic or semi-automatic approaches, the identified tumor volume would correspond with the GTV, and the CIV could then be found automatically by expanding the GTV volume by a pre-defined amount (e.g., defining the CTV as a volume that encompasses a 20 mm wide margin around the tumor).

In other embodiments, the GIN is defined as the volume of the enhancing tumor tissue, and the peritumoral boundary zone (PBZ) is defined as the white matter and grey matter voxels in a 3 mm thick volume around the following tissues: enhancing tumor, necrotic core, and resection cavity. In these embodiments, the target volume could be the joint volume of GTV and PBZ.

In other embodiments, it may be sufficient for the user to define a region of interest in which they want to optimize the power loss density as the target volume. This region of interest might be for instance a box volume, a spherical volume, or volume of arbitrary shape in the anatomic volume that encompasses the tumor. When this approach is used, complex algorithms for accurately identifying the tumor may not be needed.

In step S24, a set of model electrodes is added to the 3D model at a first set of locations with respect to the 3D model so that a simulation of the resulting electric field distribution and power loss density distribution can be calculated for that specific set of locations. In the context of glioblastoma, it is common to position one electrode array (i.e., the anterior electrode array on the forehead, one electrode array (i.e., the posterior electrode array) on the back of the head, one electrode array on the right side of the head, and one electrode array on the left side of the head. But there is considerable leeway as to the exact position for each of those electrode arrays.

In step S26, the expected power loss density (i.e., the power loss density that will be present when the first set of model electrodes positioned at the first set of locations is used to impose an alternating electric field in the target volume) is determined for each of the voxels in the target volume.

Figure 3:
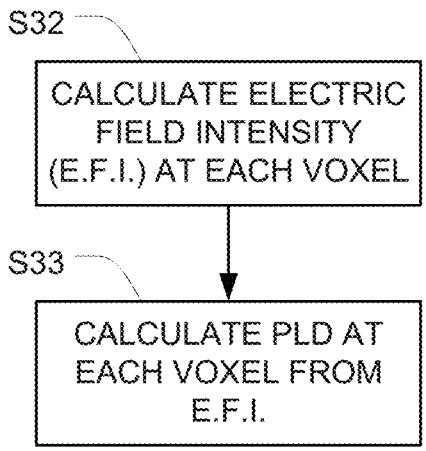
FIG. 3 depicts one approach for implementing step S26 in FIG.

FIG. 3 depicts one approach for implementing step S26 in FIG. 2 for a given set of electrode positions. In this approach, the power loss density distribution is determined using a two-step process. In the first step (S32), the electric field intensity that will be present when the first set of model electrodes is positioned at the first set of locations is used to impose an alternating electric field in the target volume is determined for each of the voxels in the body portion.

This may be accomplished, for example, by using the positions for the simulated electrodes from step S24, setting boundary conditions on the realistic body-portion model, and then calculating the electric field (e.g. using numeric simulations) that develops within the realistic body-portion model when the electrodes are placed on the realistic body-portion model at the selected position and boundary conditions applied (e.g., by applying a simulated AC voltage to the simulated electrodes).

For example, a model of the electrode arrays that will be used to apply the TTFields are placed on the realistic body-portion model (e.g., a head model). Then a volume mesh, suitable for finite element (FE) method analysis, can be created. Next, boundary conditions can be applied to the model. Examples of boundary conditions that might be used include Dirichlet boundary (constant voltage) conditions on the electrode arrays, Neumann boundary conditions on the electrode arrays (constant current), or floating potential boundary conditions that set the potential at that boundary so that the integral of the normal component of the current density is equal to a specified amplitude. The model can then be solved with a suitable finite element solver (e.g., a low frequency quasistatic electromagnetic solver) or alternatively with finite difference (FD) algorithms. The meshing, imposing of boundary conditions and solving of the model can be performed with existing software packages such as Sim4Life, Comsol Multiphysics, Ansys, or Matlab. The final solution of the model will be a dataset that describes the electric field distribution or related quantities such as electric potential within the computational model for a given set of electrode positions.

Then, in the second step (S33), the power loss density for each voxel in the target volume is calculated based on (a) the conductivity of the 3D model at the voxel and (b) the electric field intensity at the voxel. This calculation is preferably implemented using formula (1) noted above. Note that in some preferred embodiments, the electric field intensity is preferably determined for each of the voxels in the entire body portion, to facilitate running of the numeric simulations. But it is only necessary to calculate the power loss density within the smaller target volume. Of course, the power loss density can optionally be calculated within the entire body portion if so desired.

The approach described above in connection with FIG. 3 provides the power loss density for a situation where a continuous AC voltage is being applied to the simulated electrodes. But for many types of tumors, the orientation of the TTFields is switched periodically. For example, glioblastoma is typically treated using TTFields by (a) applying an AC voltage between the right and left electrodes for one second; (b) applying an AC voltage between the anterior and posterior electrodes for one second; and repeating steps (a) and (b) for the duration of the treatment. In these situations, the electric field distribution during step (a) will be different from the electric field distribution during step (b). And because power loss density is derived from the electric field, this means that the power loss density during step (a) will also be different from the power loss density during step (b). In these situations, the power loss density that is used for the numeric simulations (which will ultimately be used to determine where to position the electrodes) can be selected using an appropriate rule.

Figure 4:
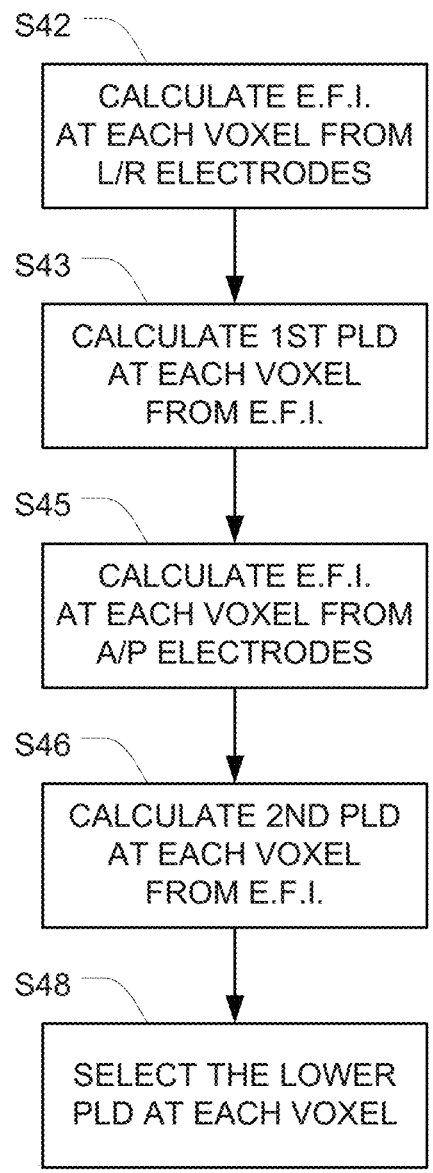
FIG. 4 depicts an example of calculating power loss density by using whichever power loss density is lowest at each voxel.

FIG. 4 depicts one example of a suitable rule that determines the power loss density at each voxel by calculating the power loss density separately for each field direction at each voxel, and using whichever power loss density is lowest at each voxel. More specifically, in step S42, the electric field intensity that will be present when the AC voltage is applied between the left and right electrodes is calculated for each voxel in the body portion. Then, in step S43, the corresponding power loss density is computed for each voxel in the target volume, e.g. using formula (1). Similarly, in step S45, the electric field intensity that will be present when the AC voltage is applied between the anterior and posterior electrodes is calculated for each voxel in the body portion. Then, in step S46, the corresponding power loss density is computed for each voxel in the target volume, e.g. using formula (1). Finally, in step S48, the lowest one of the two power loss densities that were computed for each voxel (i.e., in steps S43 and S46) is selected. The value of the power loss density selected in step S48 is then used in subsequent steps of the process.

This approach of selecting the lowest power loss density at each voxel can also be extended to embodiments in which the electric field is applied in three or more different directions at different moments in time. In these embodiments, the power loss density distribution would be calculated separately when the electric field is applied in each of the three or more directions, and the lowest of those power loss density values at each voxel would be used as the value for subsequent computations for that voxel. In alternative embodiments, a different rule (e.g., using the mean instead of the minimum) may be used when different power loss densities exist at any given voxel at different times.

Returning to FIG. 2, steps S24-S26 provide an approach for calculating the power loss density (PLD) that will be present at each voxel in the target volume for a given set of electrode positions. And in step S28, those two steps (i.e., steps S24 and S26) are repeated for one or more other sets of electrode positions. Repeating these two steps generates a separate PLD distribution for each set of electrode positions. After all these separate PLD distributions have been generated, processing proceeds to step S29, where a set of locations for the electrodes is selected based on all the generated PLD distributions. This selection may be accomplished, for example, by choosing the best PLD (e.g., as explained below) and subsequently outputting a description of the electrode positions that yielded that particular PLD.

A wide variety of approaches may be used to determine which one of the PLD distributions is best for a particular patient. In one example, whichever PLD distribution maximizes the average PLD (averaged over all voxels in the target volume) may be deemed to be the best. Alternatively, whichever PLD distribution maximizes the lowest PLD (measured over all voxels in the target volume) may be deemed to be the best. In other embodiments, a PLD distribution may be deemed suitable if the PLD averaged over all voxels in the target volume is above a given threshold (e.g., 2 mW/cm$^3$).

After the description of the electrode positions that yielded the best PLD is output, healthcare professionals can use this description to place the electrodes on the patient's heads (or other body portion). Treatment using TTFields can then proceed by applying AC voltages to the electrodes (e.g., as described in U.S. Pat. No. 7,565,205, which is incorporated herein by reference).

Optionally, steps S24-S28 may be automated by running an optimization algorithm to find the layout that yields the optimal PLD distribution within the target volume. This optimization may be implemented by identifying the volume targeted for treatment within a body-portion model (as described above in connection with step S23); automatically placing electrode arrays and setting boundary conditions on the realistic body-portion model (as described above in connection with step S24); calculating the PLD distribution that develops within the realistic body-portion model once the electrodes have been placed on the realistic body-portion model and boundary conditions applied; and running an optimization algorithm to find the layout that yields a desired PLD distribution within the target volume.

In the context of optimization, steps S24 and S26 are performed repeatedly. In each iteration, step S24 will involve automatically positioning the electrode arrays on the realistic body-portion model.

A variety of approaches can be used to find the optimal array layouts for any given patient. One example of an optimization approach is an exhaustive search. In this approach the optimizer will include a bank with a finite number of array layouts that should be tested. The optimizer performs simulations of all array layouts in the bank (e.g., by repeating steps S24 and S26 for each layout), and picks the array layouts that yield the optimal PLD distribution in the target volume.

Another optimization approach is an iterative search. This approach uses an algorithm such as minimum-descent optimization methods and simplex search optimization. Using this approach, the algorithm iteratively tests different array layouts on the body portion (e.g., the head) and calculates the PLD distribution in the target volume for each layout. This approach therefore also involves repeating steps S24 and S26 for each layout. At each iteration, the algorithm automatically picks the configuration to test based on the results of the previous iteration. The algorithm is designed to converge so that it maximizes (or minimizes) a defined target function for the PLD in the target volume.

The benefits of using power loss density to plan cancer treatment using TTFields is borne out by a retrospective analysis of the results of a clinical trial. This retrospective analysis shows that overall survival increases with increased TTFields power (mW/cm$^3$) delivered to the target volume. This analysis establishes the desirability of optimizing the positions of the electrode arrays on the patient's body for TTFields treatment by looking at power loss density in order to maximize power delivery to the tumor.

In this study, dose metrics that allow for the measurement of cumulative dose over time were defined. The connection between field modelled dose and overall survival and progression free survival within these patients was investigated. The pool of patients began with 466 patients. 379 patients remained after treatment duration of two months. MRI quality was sufficient to create models in only 317 patients. This yielded 317 total patients in the study. The following patient data was used for modelling: (1) patient MRI at baseline; (2) extent of resection (used for contouring tumor and resection cavity); (3) recommended transducer array layout as recorded in patient records; and (4) average compliance and electrical current derived from log files of devices used by patients.

TTFields were delivered in two directions during treatment using the Novocure Optune™ system. So a complete analysis needs to consider the effects of the electric field in both directions (i.e., both when the left/right electrodes are used to impose the field; and when the anterior/posterior electrodes are used to impose the field). The power loss density at each voxel was determined by determining the power loss density resulting from the left/right field, determining the power loss density resulting from the anterior/posterior field, and selecting the lower of those two power loss densities at each voxel. (This selection was based on an assumption that at each point, the channel (i.e., LR or AP) that delivers the lower dose determines the efficacy.) This parameter is referred to herein as the Local Minimum Power Density (LMiPD), and it represents the lower of the two power loss densities delivered to each point.

Figure 5A:
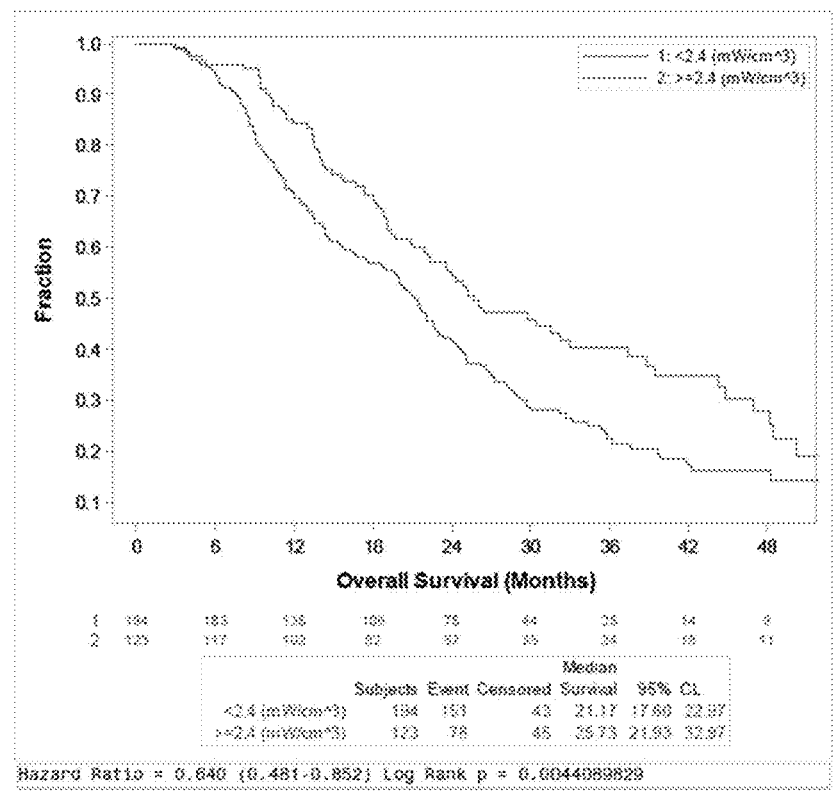
FIGS. 5A and 5B are Kaplan-Meier curves based on Local Minimum Power Density that divide test patients into two groups with the most statistically significant difference in overall survival and progression free survival, respectively.
Figure 5B:
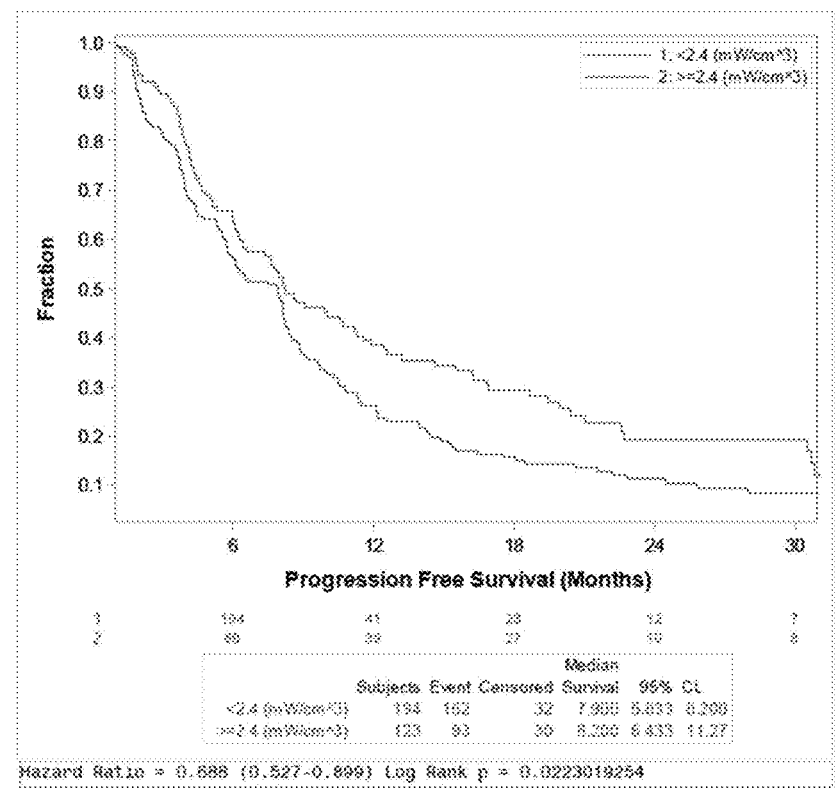

Kaplan-Meier curves were then used to find a threshold LMiPD that divides the patients into two groups with the most statistically significant difference in overall survival and progression free survival, as seen in FIGS. 5A and 5B, respectively. In each of these figures, the lower trace represents an average LMiPD in the target volume of <2.4 mW/cm$^3$, and the upper trace represents an average LMiPI) in the target volume of ≥2.4 mW/cm$^3$. This data suggests that it can be advantageous to plan treatment using TTFields so that the average LMiPD in the target volume is at least 2.4 mW/cm$^3$. In alternative embodiments, treatment using TTFields may be planned so that the average LMiPD in the target volume is at least 1.15 mW/cm$^3$. In other alternative embodiments, treatment using TTFields may be planned so that the average LMiPD in the target volume is at least 1.0 mW/cm$^3$.

Notably, TTFields were not applied to the patients in the study 100% of the time (e.g., if the TTFields were turned off while bathing or for any other reason). To account for this factor, another parameter was developed. This parameter is referred to herein as Local Minimum Dose Density (LMiDD), and it represents the LMiPD multiplied by the percentage of time that the TTFields were applied.

Figure 6A:
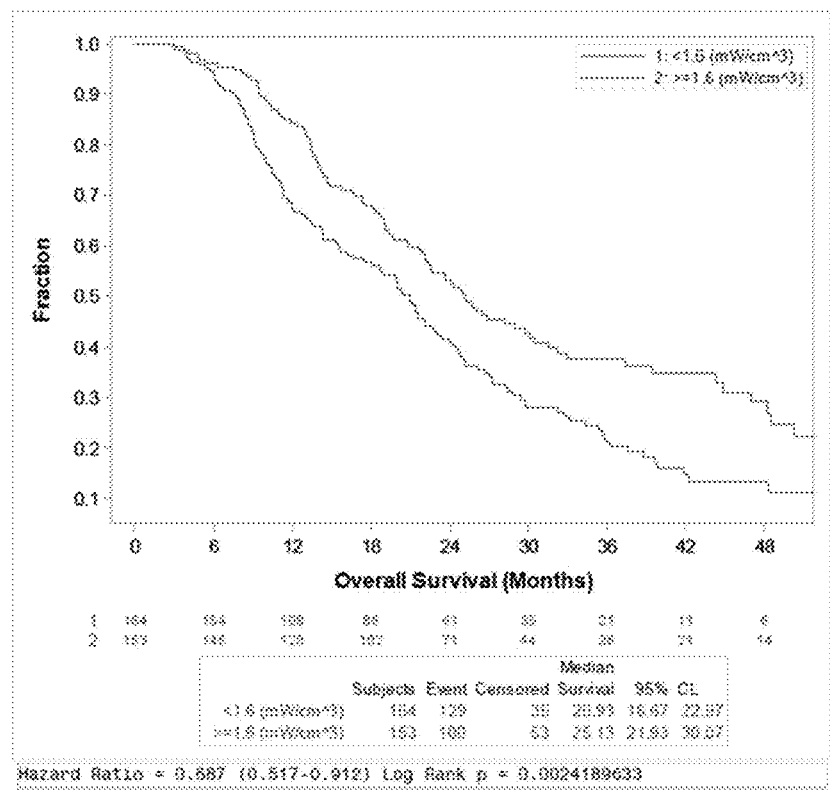
FIGS. 6A and 6B are Kaplan-Meier curves based on Local Minimum Dose Density that divide test patients into two groups with the most statistically significant difference in overall survival and progression free survival, respectively.
Figure 6B:
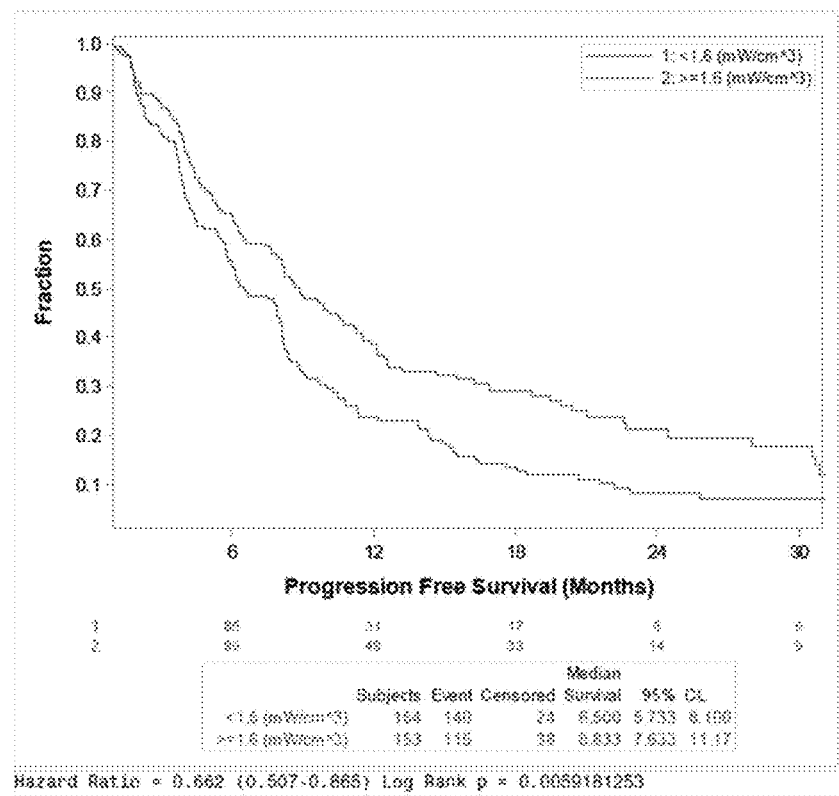

Once again, Kaplan-Meier curves were used to find a threshold. LMiDD that divides the patients into two groups with the most statistically significant difference in overall survival and progression free survival, as seen in FIGS. 6A and 6B, respectively. In each of these figures, the lower trace represents an average LMiDD in the target volume of <1.6 mW/cm$^3$, and the upper trace represents an average LMiDD in the target volume of ≥1.6 mW/cm$^3$. This data suggests that it can be advantageous to plan treatment using TTFields so that the average LMiDD in the target volume is at least 1.6 mW/cm$^3$. In alternative embodiments, treatment using TTFields may be planned so that the average LMiDD in the target volume is at least 0.77 mW/cm$^3$. In other alternative embodiments, treatment using TTFields may be planned so that the average LMiDD in the target volume is at least 0.7 mW/cm$^3$.

This analysis shows that power loss density is a viable physical measurement that can be used to accurately quantify the dose of TTFields in treatment planning.

Figure 7A:
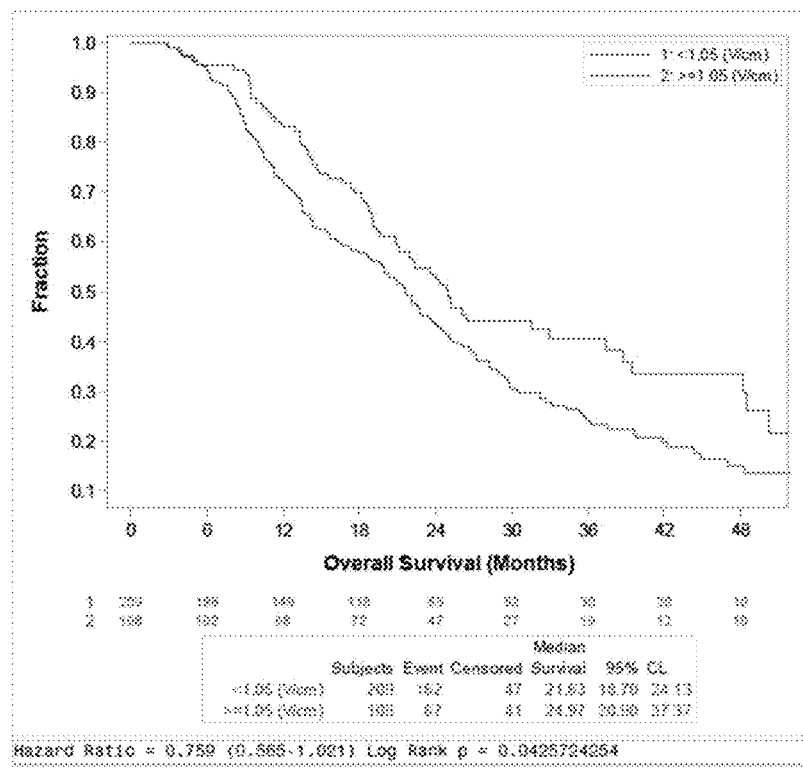
FIGS. 7A and 7B are Kaplan-Meier curves based on Local Minimum Field Intensity that divide test patients into two groups with the most statistically significant difference in overall survival and progression free survival, respectively.
Figure 7B:
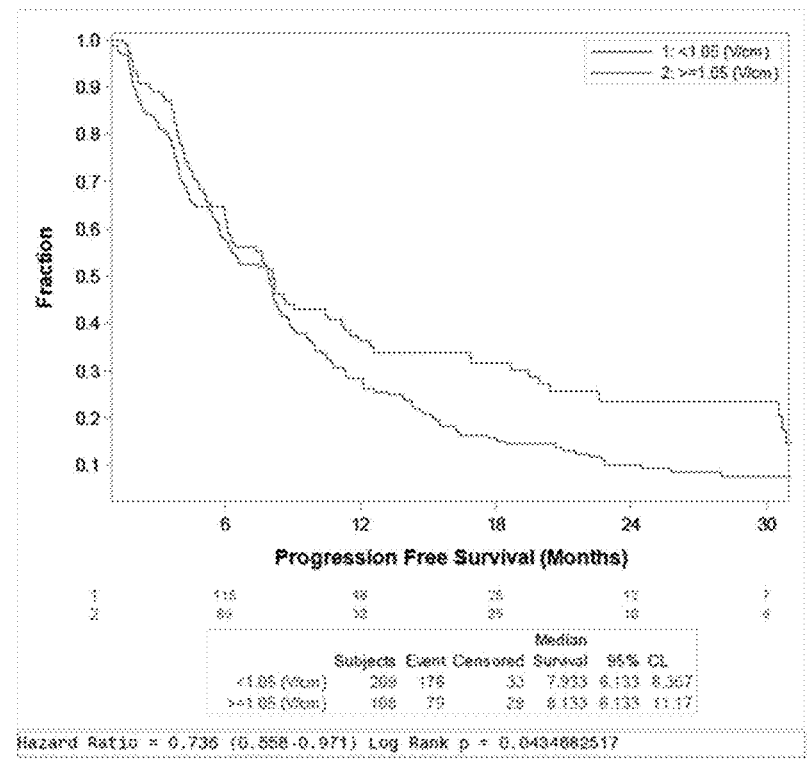

An additional parameter was also analyzed. More specifically, the Local Minimum Field intensity (LMiFI), which is the lower of the two field intensities (i.e., the lower of the LR field and the AP field) delivered to each point in the target volume. Once again, Kaplan-Meier curves were used to find a threshold LMiFI that divides the patients into two groups with the most statistically significant difference in overall survival and progression free survival, as seen in FIGS. 7A and 7B, respectively. In each of these figures, the lower trace represents an average LMIFI in the target volume of <1.05 V/cm, and the upper trace represents an average LMiFI in the target volume of ≥1.05 V/cm. This data suggests that it can be advantageous to plan treatment using TTFields so that the average LMiFI in the target volume is at least 1.05 V/cm. In alternative embodiments, treatment using TTFields may be planned so that the average LMiFI in the target volume is at least 1.0 V/cm. In other alternative embodiments, treatment using TTFields may be planned so that the average LMiFI in the target volume is at least 0.7 V/cm.

In addition, the total power loss (power delivered by TTFields to the models) was calculated. Integrating power loss density over the head in simulations revealed that the total power loss of TTFields in the head during treatment was between 20-40 watts, which is equivalent to 412-825 Kcal per day. Thus, the power delivered by TTFields is comparable or larger than the resting metabolic rate of the brain (i.e., about 20% of the body's resting metabolic rate, which is typically between 1,400 and 1,800 Kcal).

Finally, although this application relies on examples for optimizing array layouts on the head, the methods described herein can also be used for optimizing array layouts for treatment of other body regions, including but not limited to the thorax and abdomen.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of planning a treatment using alternating electric fields at a given frequency in a portion of a subject's body, the method comprising the steps of:
   (a) obtaining at least one image of the portion;
   (b) generating, based on the obtained at least one image, a 3D model of electrical conductivity or resistivity at the given frequency within the portion;
   (c) identifying a target volume within the 3D model, the target volume including a plurality of voxels;
   (d) adding a first set of model electrodes to the 3D model, with the first set of model electrodes positioned at a first set of locations with respect to the 3D model;
   (e) determining, for each of the voxels in the target volume, a power loss density that will be present when the first set of model electrodes positioned at the first set of locations is used to impose an alternating electric field in the target volume;
   (f) adding a second set of model electrodes to the 3D model, with the second set of model electrodes positioned at a second set of locations with respect to the 3D model; and
   (g) determining, for each of the voxels in the target volume, a power loss density that will be present when the second set of model electrodes positioned at the second set of locations is used to impose an alternating electric field in the target volume; and
   (h) selecting a set of locations for the electrodes based on results of step (e) and step (g),
   wherein the given frequency is between 100 kHz and 300 kHz.

2. The method of claim 1, further comprising a step of outputting a description of the selected set of locations.

3. The method of claim 1, wherein step (e) and step (g) each comprises:
   determining, for each of the voxels in the target volume, an electric field intensity that will be present when a respective set of model electrodes positioned at a respective set of locations is used to impose an alternating electric field in the target volume; and
   determining a respective power loss density for each voxel in the target volume based on the conductivity of the 3D model at the voxel and the electric field intensity at the voxel.

4. The method of claim 3, wherein the power loss density for each voxel in the target volume is determined using the formula $L=\frac{1}{2}\sigma|E|^2$, where $\sigma$ is the conductivity of the 3D model at the voxel and $|E|$ is the electric field intensity at the voxel.

5. The method of claim 1, wherein step (h) comprises selecting the set of locations that maximizes average power loss density in the target volume.

6. The method of claim 1, wherein step (h) comprises selecting the set of locations that maximizes a lowest power loss density in the target volume.

7. The method of claim 1, further comprising the steps of:
(h) adding a third set of model electrodes to the 3D model, with the third set of model electrodes positioned at a third set of locations with respect to the 3D model; and
(i) determining, for each of the voxels in the target volume, a power loss density that will be present when the third set of model electrodes positioned at the third set of locations is used to impose an alternating electric field in the target volume, and
wherein the selecting comprises selecting a set of locations for the electrodes based on results of step (e), step (g), and step (i).

8. The method of claim 1, wherein the at least one image of the portion comprises an MRI image of the portion.

9. The method of claim 1, further comprising the steps of:
affixing a plurality of electrodes to the subject's body at the selected locations; and
applying an AC voltage between the affixed electrodes, so as to impose the alternating electric field in the target volume.

10. A method of planning a treatment using alternating electric fields at a given frequency in a portion of a subject's body, the method comprising the steps of:
(a) obtaining at least one image of the portion;
(b) generating, based on the obtained at least one image, a 3D model of electrical conductivity or resistivity at the given frequency within the portion;
(c) identifying a target volume within the 3D model, the target volume including a plurality of voxels;
(d) adding a first set of model electrodes to the 3D model, with the first set of model electrodes positioned at a first set of locations with respect to the 3D model;
(e) determining, for each of the voxels in the target volume, a smaller one of first and second power loss densities that will be present when the first set of model electrodes positioned at the first set of locations is used to impose an alternating electric field in the target volume with first and second orientations, respectively;
(f) adding a second set of model electrodes to the 3D model, with the second set of model electrodes positioned at a second set of locations with respect to the 3D model; and
(g) determining, for each of the voxels in the target volume, a smaller one of first and second power loss densities that will be present when the second set of model electrodes positioned at the second set of locations is used to impose an alternating electric field in the target volume with first and second orientations, respectively; and
(h) selecting a set of locations for the electrodes based on results of step (e) and step (g),
wherein the given frequency is between 100 kHz and 300 kHz.

11. The method of claim 10, further comprising the step of outputting a description of the selected set of locations.

12. The method of claim 10, wherein step (e) and step (g) each comprises:
determining, for each of the voxels in the target volume, a first orientation electric field intensity that will be present when a respective set of model electrodes positioned at a respective set of locations is used to impose an alternating electric field in the target volume with the first orientation;
determining a respective first-orientation power loss density for each voxel in the target volume based on the conductivity of the 3D model at the voxel and the first orientation electric field intensity at the voxel;
determining, for each of the voxels in the target volume, a second orientation electric field intensity that will be present when the respective set of model electrodes positioned at the respective set of locations is used to impose an alternating electric field in the target volume with the second orientation;
determining a respective second-orientation power loss density for each voxel in the target volume based on the conductivity of the 3D model at the voxel and the second orientation electric field intensity at the voxel; and
selecting, for each of the voxels in the target volume, the smaller of the respective first-orientation power loss density and the respective second-orientation power loss density.

13. The method of claim 12, wherein the respective first-orientation power loss density and the respective second-orientation power loss density for each voxel in the target volume is determined using the formula $L=\frac{1}{2}\sigma|E|^2$, where $\sigma$ is the conductivity of the 3D model at the voxel and $|E|$ is the respective electric field intensity at the voxel.

14. The method of claim 10, wherein step (h) comprises selecting the set of locations that maximizes average power loss density in the target volume.

15. The method of claim 10, wherein step (h) comprises selecting the set of locations that maximizes a lowest power loss density in the target volume.

16. The method of claim 10, further comprising the steps of:
(h) adding a third set of model electrodes to the 3D model, with the third set of model electrodes positioned at a third set of locations with respect to the 3D model; and
(i) determining, for each of the voxels in the target volume, a smaller one of first and second power loss densities that will be present when the third set of model electrodes positioned at the third set of locations is used to impose an alternating electric field in the target volume with first and second orientations, respectively, and
wherein the selecting comprises selecting a set of locations for the electrodes based on results of step (e), step (g), and step (i).

17. The method of claim 10, wherein the at least one image of the portion comprises an MRI image of the portion.

18. The method of claim 10, further comprising the steps of:
affixing a plurality of electrodes to the subject's body at the selected locations; and
applying an AC voltage between the affixed electrodes, so as to impose the alternating electric field in the target volume.

19. The method of claim 10, wherein the treatment using alternating electric fields is planned so that an average Local Minimum Power Density in the target volume is at least 1.0 mW/cm$^3$.

* * * * *